United States Patent [19]

Smits et al.

[11] Patent Number: 4,764,234

[45] Date of Patent: Aug. 16, 1988

[54] METHOD OF APPLYING ADHESIVE

[75] Inventors: Donald M. Smits; Patrick J. Daley, both of Green Bay, Wis.; Mary E. Buckley, Wheeling, Ill.

[73] Assignee: The Kendall Company, Boston, Mass.

[21] Appl. No.: 943,990

[22] Filed: Dec. 18, 1986

[51] Int. Cl.4 .............................................. B31F 1/22
[52] U.S. Cl. .................................. 156/164; 118/241; 118/323; 118/674; 118/681; 156/244.11; 156/356; 156/578
[58] Field of Search ............... 156/164, 578, 356–357, 156/244.11; 118/216, 219, 221, 222, 669, 674, 680, 681, 323, 241

[56] References Cited

U.S. PATENT DOCUMENTS

| | | | |
|---|---|---|---|
| 4,495,890 | 1/1985 | Nikkel et al. | 118/674 |
| 4,610,745 | 9/1986 | Sallee et al. | 156/164 X |
| 4,618,384 | 10/1986 | Sabee | 156/205 |

Primary Examiner—David Simmons
Attorney, Agent, or Firm—Donald Halgren

[57] ABSTRACT

The method of manufacturing an absorbent pad for utilization as a diaper or an adult incontinent brief, wherein a pair of continuous bands of adhesive are applied to the backing sheet of the pad, prior to assembly thereof. The nozzles eject adhesive onto a moving web comprising the backing sheet. The nozzles are shifted sideways during their extrusion of adhesive, from a first location to a second location, thus generating a pair of non-linear bands of adhesive on the backing sheet. The nozzles are again shifted from their second location to their original first location upon receipt of proper signals from a control mechanism. The elastic band is not shifted when the nozzles are, thus effectuating securement of the elastic bands only on the portions of the backing sheets where the adhesive was applied at the first location.

5 Claims, 5 Drawing Sheets

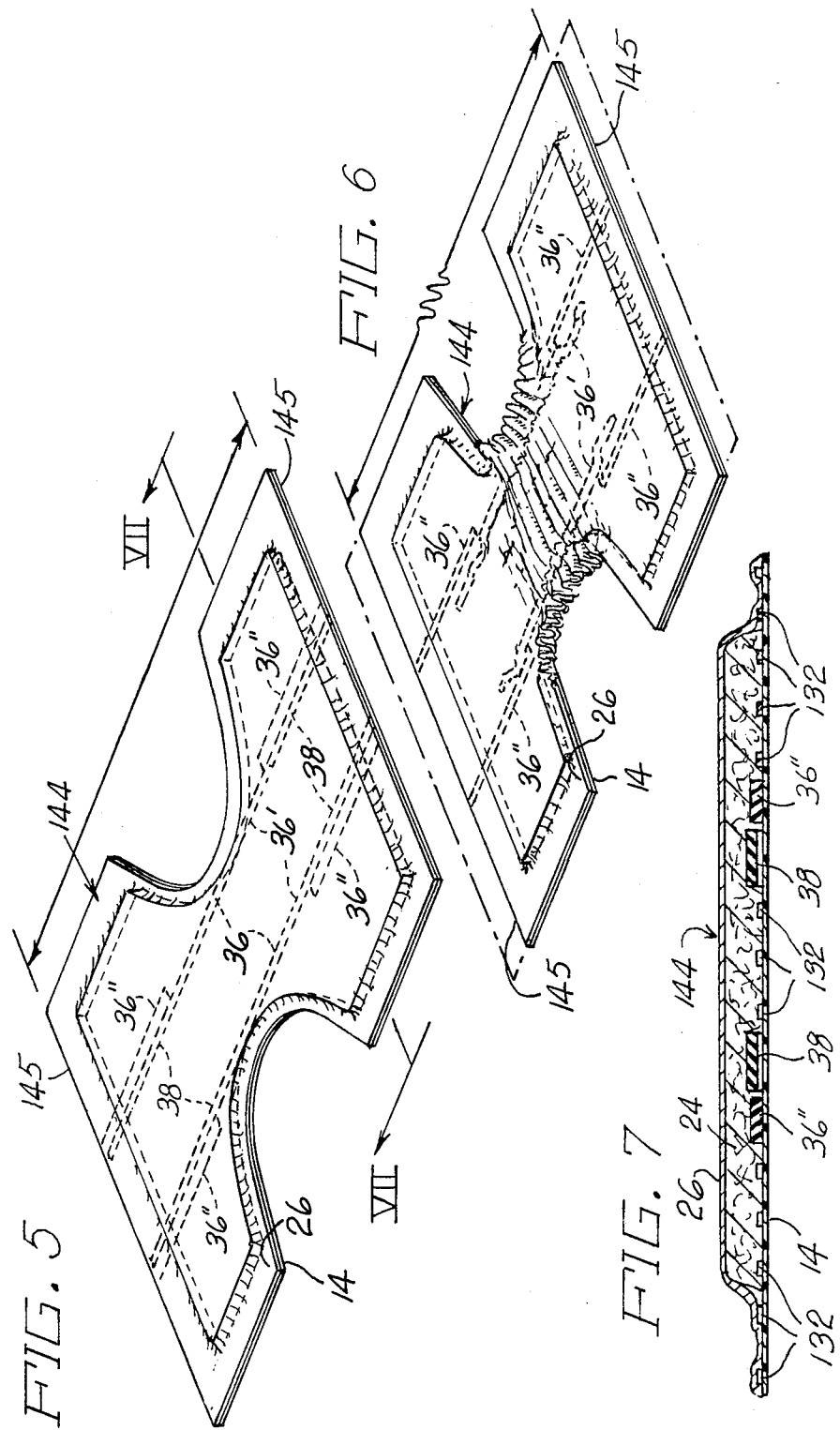

METHOD OF APPLYING ADHESIVE

BACKGROUND OF THE INVENTION

(1) Field of the Invention

This invention relates generally to the method of making an absorbent pad, and particularly on the method of continuously applying adhesive for securing elastic bands thereto.

(2) Prior Art

Elastic ribbon should be applied in a stretched condition to the leg portions of absorbent undergarments such as babies' diapers or adult continent briefs. The elastic ribbon is applied in a stretched condition only in that leg portion so as to cause gathers therein. The remaining portion of the elastic extending over the balance of the absorbent pad is not adhered to the pad, so that that portion of the pad will not gather. In the manufacture of diapers and absorbent pads as well as adult incontinent briefs, an elastic band is continuous form is placed against an unrolled web or a continuous web or backing material. The elastic band has adhesive applied thereon in discontinuous portions therealong, so as to effectuate the attachment of the bands to the backing material along the leg portions thereof. Such an apparatus and method for same is shown for example, in U.S. Pat. No. 4,081,301. Adhesive, as shown in this Patent, may be applied in thin strands on the elastic or as individual dots of adhesive on the elastic. The elastic band is then applied to diaper material as the diaper material proceeds along the assembly processes. As the individual backing sheets are cut and severed from one another, the stretched elastics are also severed. The portion of the elastics that are glued or bound by adhesive to the backing sheet of the diaper cause the diaper in that portion to gather. The unattached portion of the rubber band merely remain in the flaccid state adjacent the absorbent pad. U.S. Pat. No. 4,371,417 shows an apparatus for inserting elastic strips onto diapers for stretching and relaxing predetermined lengths of the elastic strips as they are secured to the diaper material. U.S. Pat. No. 4,297,157 shows a rather complicated apparatus for placing elastic strips under tension, onto garments. An annular array of linkages and arms are used to apply the elastic to discrete areas adjacent the leg openings of diapers.

Another Patent showing the adhesion of elastic to disposable diapers is shown in U.S. Pat. No. 4,585,507. An oscillating fork means V-folds longitudinally spaced portions of an adhesive equipped ribbon against the backing sheet of a diaper. The V-shaped longitudinally spaced portions do not adhere to their respective portions of diaper and so fail to cause the required gathering thereof. U.S. Pat. No. 4,578,133 shows a method and apparatus for applying strips of elastic to a web of diaper material. The apparatus is very complicated and requires a difficult method of applying the strips to the web of material. Two other recent disclosures are shown in U.S. Pat. Nos. 4,572,043 and 4,574,022 which again also show rather complicated apparatus for applying discrete lengths of elastic material to a moving web of backing sheet. In U.S. Pat. No. 4,525,229 an elastic band is attached to a tape which is attached to the web forming the backing sheet of the diaper. U.S. Pat. No. 4,556,596 shows self adhering elastic strips applied to a flexible base material. U.S. Pat. No. 4,543,141 shows another arrangement for longitudinally folding portions of the ribbon prior to its disposition against a base sheet to immobilize those portions of the ribbon. U.S. Pat. No. 4,523,969 shows an arrangement for gripping elastic ribbon at several points and stretching same prior to its application against a base sheet comprising the bottom portion of the diaper. U.S. Pat. No. 4,507,163 shows a method of feeding adhesive onto an elastic before it is applied to the base of a diaper.

Though the collection of prior art is numerous, and often very complicated, none of it appreciates a simpler method of performing the same operation.

Thus it is an object of the present invention to provide a method of attaching the elastic to a web not shown in the art.

It is a further object of the present invention to provide a controllable, continuous application of adhesive to a backing sheet of a diaper or an adult brief.

BRIEF SUMMARY OF THE INVENTION

The present invention provides for continuously attaching continuous lengths of elastic ribbon to a moving web of indeterminate length. The elastic ribbon is of continuous length, and is applied against a continuous strip of adhesive placed upon the moving web. The continuous strip of adhesive is applied on a nonlinear manner to the moving web. The web which may comprise the back sheet of a diaper or an adult incontinent brief, or the like, is caused to move about on a rotatable roller or drum. Subsequent to the web moving on the roller it is caused to travel upon a conveyor belt where it meets an upper layer of fluff material and a topmost layer. As the web moves around the roller, a pair of adhesive ejection nozzles apply a continuous strip of adhesive directly to the moving web. The nozzles are shifted transversely during the application of the strip of adhesive onto the moving web so as to effect a generally stepped or "sinusoidal" pattern of adhesive thereon.

The method of the present invention comprises feeding an elastic ribbon to an assembly station in a stretched condition; supplying a continuous web of material such as backing sheet to an assembly station in a tensioned condition; feeding an elastic ribbon to the assembly station in a stretched condition; applying adhesive in a continuous manner to the web of material; moving transversely the adhesive application nozzles while said web is moving; returing said adhesive applying nozzles to their original position while said web is moving; and timing the movement of the adhesive applying nozzles in conjunction with the speed of the moving web so as to properly effectuate a generally stepped repetitive pattern of adhesive thereon. Finally, the elastic ribbons are attached to portions of the adhesive bands that is applied to the backing sheet as it goes around the roller.

The apparatus at the assembly station for manufacturing the absorbent web of material comprises a rotatable roller of drum supported on an axis. The rotatable drum has a first idler roll supported thereabove. A web of backing material of a indeterminate length is disposed over the first idler roll and around the drum. The web of material is continued over a second idler roll and arranged to be continuously transported on a conveyor belt on which it receives a layer of absorbent fluff material and a top sheet. An adhesive applying mechanism is disposed adjacent the drum so as to apply a pair of continuous strips or bands of adhesive against the web as it wraps around the drum.

The adhesive applying mechanism comprises a lower frame. The lower frame consists of a pair of upstanding legs across which is disposed a transverse mounting plate. The mounting plate is generally parallel to the axis of the drum. A first moving means is fixedly attached to the generally mid-portion of the mounting plate and is attached to the movable portion of the first moving means. The moving means may comprise a double acting air cylinder. A middle plate is movedly disposed above the mounting plate. A support means is arranged on each end of the middle plate. The support means permits the middle plate to be moved transversely with respect to the mounting plate therebeneath. A linkage is arranged between the double acting air cylinder and the middle plate so as to effect said movement.

A pair of upper plates are movably supported on the middle plate. Each upper plate carries an adhesive nozzle. Each upper plate is adjustably moveable generally longitudinally, with respect to the middle plate. Each upper plate has a manual adjustment means so as to permit the setting of the initial location of the upper plate with respect to the middle plate. Each upper plate has a second moving means thereon, such as a double acting pressure cylinder thereon. The pressure cylinder may be attached to the adhesive nozzle by a connecting rod. Each adhesive nozzle is permitted to slide transversely with respect to the upper plate. Each pressure cylinder on the upper plate is connected by proper means to a solenoid valve means which effectuates enactment of transverse movement of the adhesive nozzles with respect to the upper plates on which they are slidably disposed.

The first moving means on the lower mounting plate is connected to a pressurizable source controlled by a solenoid valve for actuating the air cylinder therewith. The first moving means effectuates movement of the middle plate and therefore the movement of the adhesive nozzles radially toward and away from the drum on which the web is carried. The adhesive nozzles, being heated, are of necessity moved away from the web of material when the web of material has stopped moving, so as to prevent any burn through thereof. A proper control system effectuates the timing of the second moving means so as to control the transverse movement of the adhesive nozzles while they are depositing a strip of adhesive onto the web or backing sheet of material as it is moved about the drum. A pair of arms extend down from the transversely immovable middle plate. At the distal end of each arm there is disposed a pulley. The pulley guides the elastic strip prior from its supply roll to its linear disposition on the adhesive strip and alternatively, to the non-adhesive portion of the web or backing sheet.

When each of the adhesive nozzles have moved transversely outwardly, they are still caused to continuously deposit the strip or bands of adhesive out of the normal path of the elastic bands. As the web of material is driven around the drum, and the elastic bands are held thereagainst, that portion of the elastic bands which are not in abutting contact with the adhesive strip on the web, will not stick to the web. Therefore the elastic band in those noncontacting, nonadhering areas will not cause the absorbent material to "gather" thereon when the elastic band has been cut and hence when it returns to its stretched state.

The absorbent pad manufactured by the apparatus and method described hereabove has a pair of adhesive strips which are disposed outwardly from their linear paths, on each side of the leg cut-out portions. Thus the adhesive strips or bands form a generally stepped configuration, the adhesive acting to secure the fluff layer against the bottom layer of the pad, where the adhesive is not contacting any elastic band. The adhesive thereby also acts as a fluid barrier to help minimize fluid migration into the side flaps of the pad, diaper or brief. The fluid, such as urine, is thereby directed along the mid-portion of the pad, helping to minimize leakage and uncomfortability in the pad.

BRIEF DESCRIPTION OF THE DRAWINGS

The objects and advantages of the present invention will become more apparent, when viewed in conjunction with the following drawings, in which:

FIG. 5 shows a perspective view of an absorbent pad indicating the pattern of adhesive strip thereon and the elastic band thereattached;

FIG. 6 shows a perspective view of the absorbent pad of FIG. 5, in an unstretched state; and FIG. 7 is a view taken along the lines VII—VII of FIG. 5.

DESCRIPTION OF THE PREFERRED EMBODIMENTS

Figure 1:
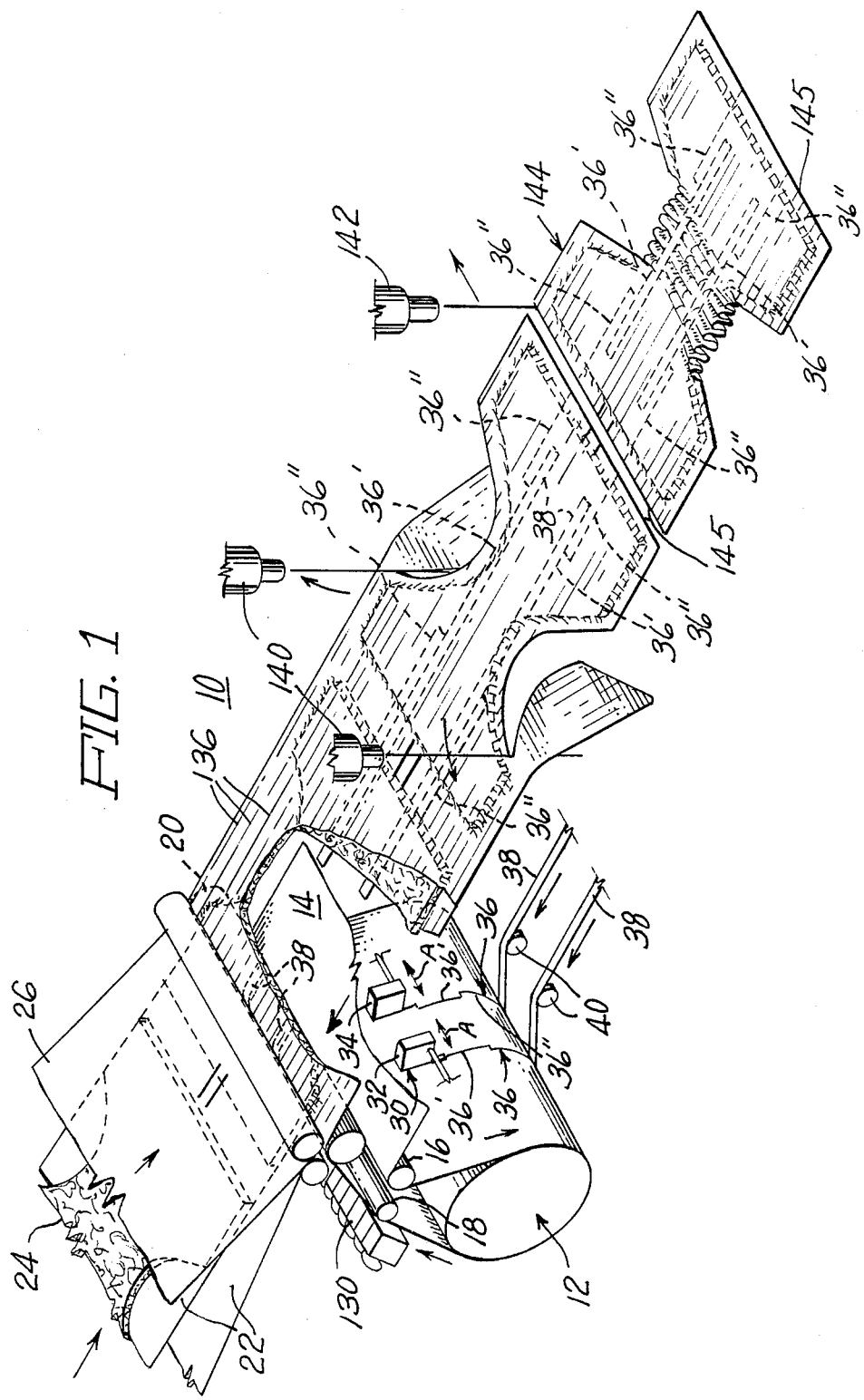
FIG. 1 is a perspective view of an assembly station of the present invention having a pair of oscillatable glue guns shown disposed against a backing sheet.

Referring to the drawings in detail, and particularly to FIG. 1, there is shown an assembly station 10, utilizable in the manufacture of absorbent pads such as baby diapers or adult incontinent briefs. This application incorporates by reference, copending U.S. patent application Ser. Nos. 944,054 and 944,056.

A rotatable roller or drum 12 is shown in perspective, having a web 14 of indeterminate length, comprising "backing material" movably disposed therearound. The web 14, moving in a direction as indicated by the arrows thereon, is coming from a source, such as a supply roll, not shown. The web 14 first passes over a first idler roll 16, before it wraps around the drum 12. The web 14 then passes over a second idler roll 18 before it begins its journey on a main conveyor belt system 20, only a portion being shown for clarity.

A feed conveyor belt system 22, is shown on the left, in FIG. 1, wherein a layer of absorbent fluff material 24 and a liquid permeable top sheet 26 are juxtaposed in contacting overlying relationship with the web 14 of backing material. The web 14 of backing material is made of a plastic or like liquid-impermeable material.

A primary adhesive applying mechanism 30, comprising a pair of movable nozzles 32 and 34, are arranged so as to apply a generally stepped array of adhesive portions comprising a non-linear strip of adhesive 36 on the web 14 as it winds around the drum 12. A pair of arrows "A" show the transverse motion available to the movable nozzles 32 and 34. Only the nozzles 32 and 34 of the adhesive applying mechanism 30 are shown for clarity, in FIG. 1.

A pair of elastic bands 38 is shown, being guided over a pair of pulleys 40. The pulleys 40 are rotatively held on the lower ends of a pair of arms 41. As the drum 12 is caused to rotate (clockwise as shown in the drawings), the elastic bands 38 are caused to be pressed against portions of the strip of adhesive 36 already deposited on the advancing web 14. The elastic bands 38 are thus fixedly attached only to those linear portions of the web 14, where the adhesive strips 36 are in line with the elastic bands 38, such as the linear strip of adhesives shown in FIG. 1 at 36'. The elastic bands 38, being held in a linear manner as the drum 12 rotates, comes into non-adhering contact with the web 14 (backing sheet), because the strip of adhesive 36, such as indicated by 36" is not in contact or alignment therewith, by virtue of the movable nozzles 32 and 34 having been actuated to their respective sides (left and right).

Figure 2:
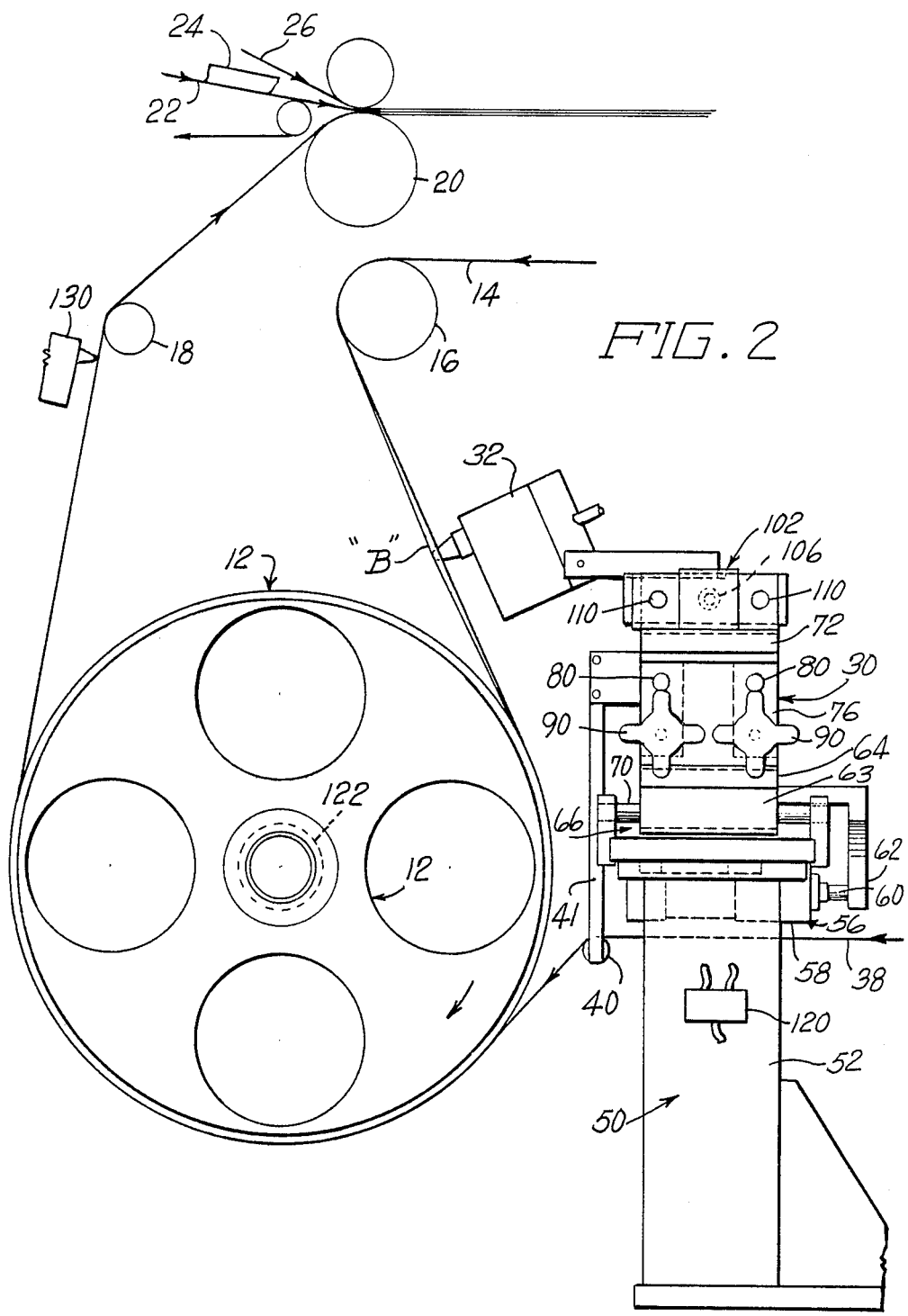
FIG. 2 is an elevational view of the end of the drum and adhesive application apparatus.
Figure 3:
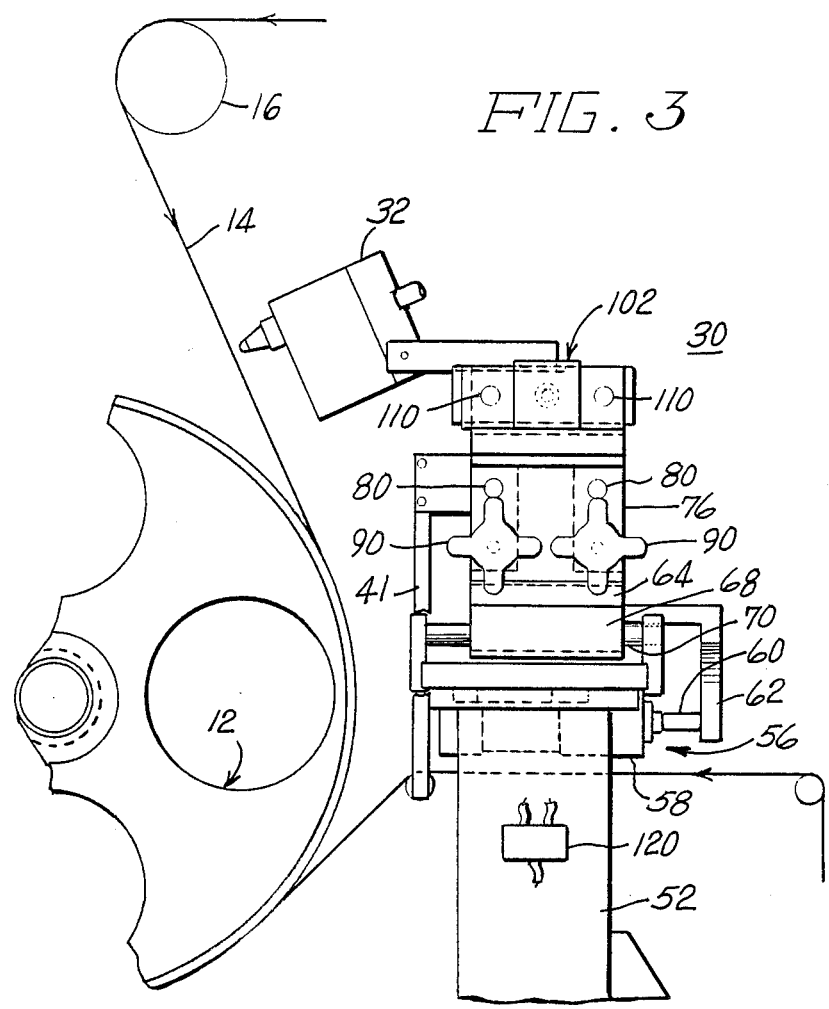
FIG. 3 is a view similar to FIG. 2, with the application apparatus moved away from the drum.
Figure 4:
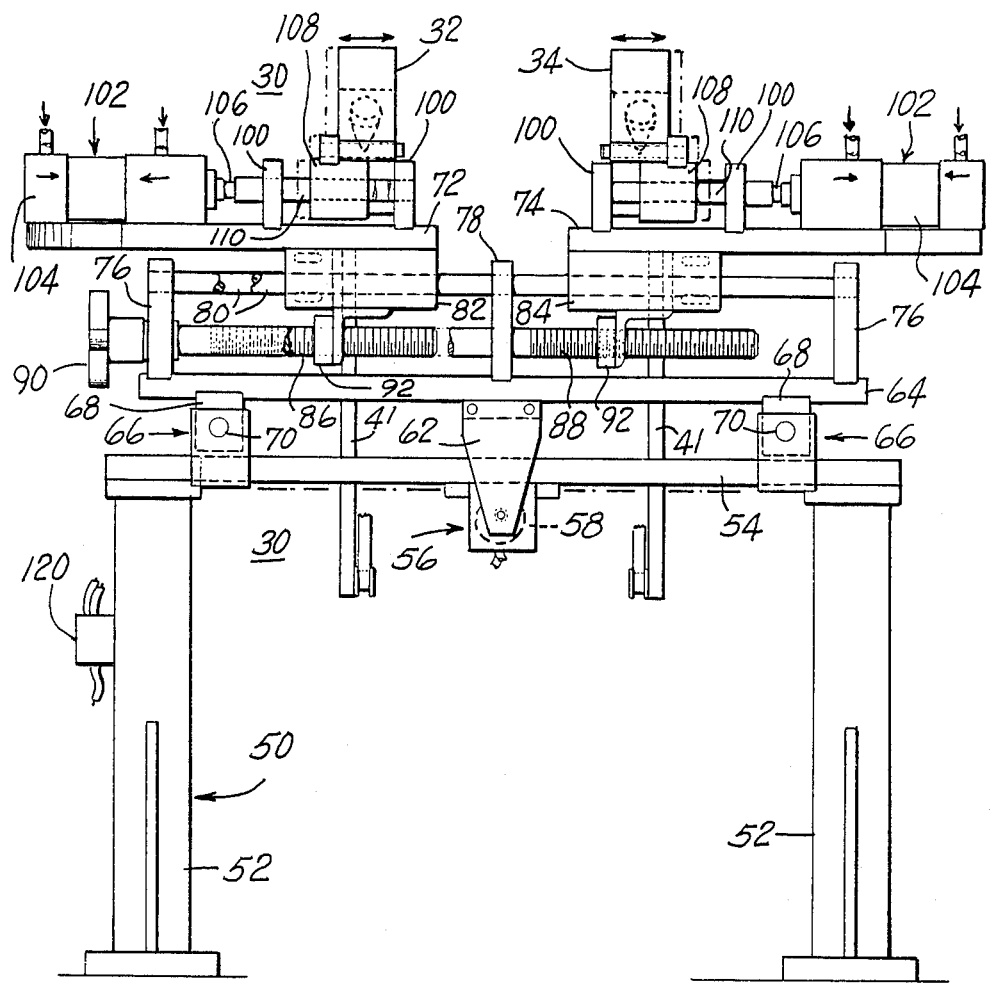
FIG. 4 is a side elevational view of the adhesive application apparatus.

The adhesive applying mechanism 30 is shown more clearly in FIGS. 2, 3 and 4. The mechanism 30 is elongated, and as such, is generally parallel to the axis of rotation of the drum 12. The adhesive applying mechanism 30 has a lower frame 50, having a pair of upstanding legs 52, across which there is disposed, a transverse mounting plate 54. The mounting plate 54 is shown most clearly in FIG. 4. A first moving means 56 is secured to the mid-portion of the mounting plate 54. The first moving means 56 may comprise a double-acting pressurizable cylinder 58, having a piston rod 60 extending therefrom. The piston rod 60 is attached to a bracket 62 extending downwardly from a middle plate 64. A support means 66, is arranged on each end of the middle plate 64. Each support means 66 comprises a slider 68 arranged to move back and forth on a bar 70.

A pair of upper plates 72 and 74 are movable supported above the middle plate 64. An end frame 76 extends upwardly from each end of the middle plate 64, and a guide frame 78 extends upwardly from the middle of the middle plate 64. A pair of slide shaft 80 are arranged between the end frames 76 and extend through the guide frame 78. Each upper plate 72 and 74 has a housing 82 and 84 respectively which is supported on and slides upon the slide shafts 80. A pair of rotatable threaded shafts 86 and 88 are disposed through one end frame 76 on one side of the middle plate 64, as shown in FIG. 4. Each threaded shaft 86 and 88 has a handle 90, by which they may be rotated. A captive nut 92 is secured to the bottom of each housing 82 and 84. Rotation of the handles 90, will rotate each threaded shaft 86 and 88, each with respect to its captive nut 92, so as to cause sliding movement, for transverse manual adjustment, of the upper plates 72 and 74 and hence their respective nozzles 32 and 34, with respect to the middle plate 64. Each arm 41 supporting the pulleys 40 are attached at their upper end, to one of the upper plates 72 or 74. Adjustment of the nozzles 32 by adjustment of the handles 90 will concomitantly adjust the pulleys 40, and thereby, the location of the elastic bands 36.

Each nozzles 32 and 34 is also arranged for transverse sliding movement on their respective upper plates 72 and 74. A pair of nozzles support frames 100 extend upwardly from each upper plate 72 and 74.

A nozzle shifting means 102 is arranged on each upper plate 72 and 74 to effectuate the transverse movement of the nozzles 32 and 34 thereon. The shifting means 102 in this embodiment preferably comprises a pressurizable double acting piston and cylinder unti 104 secured to the distalmost ends of each upper plate 72 and 74. A piston rod 106 extends movably through its outermost respective support frame 100. The piston rod 106, is attached at its distalmost end, to a nozzle bracket 108. A pair of nozzle support rods 110 are arranged between each pair of nozzle support frames 100. The nozzle brackets 108 each slide on their respective nozzle support rods 110.

Each nozzle 32 and 34 has a heating element, not shown, arranged therewithin, so as to maintain the adhesive supplied thereto, in a fluid state. Each nozzle 32 and 34 has proper adhesive supply means, under pressure, to permit a continuous ejection of adhesive onto the "backing" sheet web 14 as it moves therepast.

Each piston and cylinder unit 104 is connected through proper means, not shown, to a regulator 120, such as a solenoid valve arrangement. The regulatoe 120 provides the means for controllably shifing each adhesive nozzle 32 and 34 transversely, so as to effectuate the non-linear (almost sinusoidal) stepped pattern of adhesive onto the web 14. The regulator 120, which provides the pressure to the proper portion of the piston and cylinder units 104, is controlled by a signal generator means 122, which is arranged on the drum 12. The signal generator means 122 sends signals to a counter, not shown, which provides the input to the regulator 120, switching the valving therein to effectuate proper transverse movement of the nozzles 32 and 34. The regulator 120 may also effectuate energization of the first moving means 56 to cause the middle plate 64 to move toward or away from the drum 12 and web 14. This is presented in FIG. 3, wherein the nozzle 32 is shown withdrawn from the surface of the web 14. Whenever the web 14 is not moving, a signal may be sent to the regulator 120 to pressurize the piston-cylinder units 58 to move the nozzles 32 and 34 away from the web 14, so that they will not burn through or melt the plastic (typically) web 14. When the web 14 is not moving, the nozzles 32 and 34 are held away from the web 14, so that they will not burn through or melt plastic (typically) web 14. When the web 14 is actually moving, the nozzles 32 and 34 are pressed slightly against the web 14 for positive contact, as shown by the slight bulge "B" in the web 14, in FIG. 2.

A secondary arrangement of adhesive applying nozzles 130 is shown in FIGS. 1 and 2. The secondary nozzles 130 distribute a linear array of thin strands of adhesive 132 across the entire web 14 as shown in FIG. 1 and 7. The thin strands of adhesive 132 are utilized to help secure the layer(s) of fluff 24 against the web 14 (backing sheet), and to secure the peripheral portions of the top sheet 26 to the web 14 (backing sheet).

The assembly of absorbent pads such as diapers and adult incontinent briefs is shown in a somewhat simplified manner in FIG. 1. The fluff 24, having an "hour glass" configuration, which defines the "leg" portions, is secured between the "backing" sheet web 14 and the upper layer 26 as they proceed onto the main conveyor belt system 20. At this conjuncture, the elastic bands 38 are still maintained in a "stretched" condition while the adhesive that portion of it are placed against, sets. A leg area cutting means 140, performs a cutting operation on the backing web 14 and the upper sheet 26 so as to create the "hourglass" configuration on all the remaining layers of the absorbent pad.

A transverse cutting means 142 makes a cut across the continuous line of layers of web 14, fluff 24 and top sheet 26 at proper timed intervals to define a "waist" edge 145, and to create individual absorbent pads 144, such as diapers or adult incontinent briefs from the oncoming indeterminate length of same proceeding down the conveyor system 20.

Once the transverse cut has been made, the elastic bands 38 are no longer under tension that portion of the elastic bands 38 which was placed over the adhesive 36' which was in alignment therewith, and thus contracts to form "gathers" in the absorbent pad 144, as shown on the right hand side of FIG. 1, and in FIG. 6. The remaining elastic band 38 merely becomes loose and flaccid.

The remaining adhesive 36 to which no elastic band is attached, provides a strong bond with the fluff 24, as shown in FIG. 7. This bond with the fluff 24 extends in a generally parallel manner up both sides of the absorbent pad 144, to the waist edge 145. That extended band of adhesive 36" becomes a moisture dam to facilitate directional flow of urine away from the sides of the absorbent pad 144 where it might tend to leak.

Thus the continuous non-linear band of adhesive arranged on the backing sheet of the absorbent pad 144 provides a multiple function. It permits the elastic band 38 to be adhered to the pad where it is necessary, thus providing the "gathers" therein for snug fit around a wearer's legs, while also permitting a liquid damming function to occur, so as to direct urine from potential areas which are prone to leakage.

We claim:

1. The method of manufacturing an absorbant pad by applying a plurality of non-linear continuous bands of adhesive to a continuous moving web by an adhesive applying machine, comprising the steps of:
   passing the web around a rotatable drum;
   identifying the amount of web going by the adhesive applying machine;
   ejecting adhesive from a nozzle arrangement onto a web moving therepast;
   moving said nozzle arrangement from a first location to a second location during motion of a web therepast and during said ejection of adhesive thereon;
   returing said nozzle arrangement from said second location to its first location as a web moves therepast;
   continuing said cyclical movement of said nozzle arrangement based upon the movement of a web therepast;
   directing the transverse movement of each nozzle in the nozzle arrangement to move in opposite directions synchronously; and
   applying elastic bands continuously against said web, the bands adhering only to portions of said continuous adhesive bands.

2. The method of manufacturing an absorbent pad by applying adhesive as recited in claim 1, including:
   moving the adhesive apparatus away from any web when the web stops moving.

3. The method of manufacturing an absorbent pad applying an adhesive as recited in claim 1, including:
   moving the adhesive apparatus towards web on the drum when the web begins movement.

4. The method of manufacturing an absorbant pad, by applying a continuous band of adhesive to a backing sheet therefor, for the intermittent attachment of a continuous elastic band thereto, comprising the steps of:
   running a continuous web of backing material adjacent a pair of movable adhesive nozzles;
   measuring the movement of the web in relation to the adhesive nozzles;
   ejecting adhesive from said nozzles onto said moving web;
   moving the nozzles sideways from a first location a limited amount to a second location so as to form a pair of non-linear beads of adhesive onto said moving web;
   holding the nozzles at their "away" position for a desired period of time;
   returning the nozzles a limited amount so as to return them to their first location;
   running a pair of continuous ribbons of elastic onto said moving web; and
   attaching said ribbons of elastic onto said moving web where said nozzle has extruded adhesive thereon, in alignment with the nozzles first location.

5. The method of manufacturing an absorbent pad as recited in claim 4, including:
   permitting said ribbon of elastic to be free of attachment to said web where said nozzles have ejected adhesive thereon at their second location.

* * * * *